United States Patent [19]

Eisenberg

[11] Patent Number: 4,654,165

[45] Date of Patent: Mar. 31, 1987

[54] MICROINGREDIENT CONTAINING TRACER

[75] Inventor: Sylvan Eisenberg, San Francisco, Calif.

[73] Assignee: Micro Tracers, Inc., San Francisco, Calif.

[21] Appl. No.: 723,753

[22] Filed: Apr. 16, 1985

[51] Int. Cl.[4] .................... G01N 33/02; G01N 33/44; G01N 37/00
[52] U.S. Cl. .................... 252/408.1; 426/98; 426/97; 426/74; 436/56; 252/965
[58] Field of Search .......... 252/408.1, 1, 965; 436/2, 56; 149/123; 426/74, 89, 98, 91

[56] References Cited

U.S. PATENT DOCUMENTS

| | | |
|---|---|---|
| 2,868,644 | 1/1959 | Eisenberg . |
| 3,469,990 | 9/1969 | Eisenberg . |
| 3,772,200 | 11/1973 | Livesay .................... 149/123 X |
| 3,861,886 | 1/1975 | Meloy .................... 252/965 X |
| 4,152,271 | 5/1979 | Eisenberg . |
| 4,188,408 | 2/1980 | Eisenberg . |
| 4,363,678 | 12/1982 | Nishimura et al. ............. 149/123 X |

FOREIGN PATENT DOCUMENTS 0085414  8/1983  European Pat. Off. ............ 149/123

Primary Examiner—John F. Terapane
Assistant Examiner—S. Wolffe
Attorney, Agent, or Firm—Malcolm B. Wittenberg

[57] ABSTRACT

A tracer particle for determining the concentration of a microingredient in a bulk material is disclosed. The tracer particle comprises a finely divided ferromagnetic particulate material approximately 90% of which is approximately 325 mesh or smaller, a microingredient and a binder wherein the microingredient and ferromagnetic material are entrapped in the binder and wherein the tracer particle is approximately 35 to 80 mesh in size.

15 Claims, No Drawings

MICROINGREDIENT CONTAINING TRACER

TECHNICAL FIELD OF INVENTION

The present invention relates generally to Applicant's prior U.S. Pat. Nos. 2,868,644; 3,469,990; 4,152,271 and 4,188,408. Various microingredients, such as drugs, nutrients or other minor functional ingredients, often times require analysis for quality control or for regulatory purposes. The present invention deals with means for conveniently and effectively tracing the quantity of specific microingredients in a generally homogeneous admixture of such ingredients in a bulk material.

BACKGROUND OF THE INVENTION

It is often times imperative to be able to monitor the relative quantities of a microingredient, such as a drug or nutrient, in a bulk material for a number of reasons. For example, the United States Food and Drug Administration provides for the addition of selenium in the form of sodium selenite or selenate to certain animal feeds, but only if it is added as a premix containing not more than 200 ppm selenium. In that selenium at relatively low concentrations in feeds (i.e., 5 ppm) is exceedingly toxic, the Food and Drug Administration requires that each batch of animal feed premix be analyzed for selenium content, which is, needless to say, a laborious and time-consuming task. As such, it is clearly useful to develop a method that would permit a specific microingredient to be readily separated from the bulk material, so that it could then be analyzed free from those analytical interferences generally contributed by the bulk material. As concerns selenium such a method would permit the determination of selenium as the FDA-permitted selenite or selenate. No existing analytical procedure distinguishes selenite and selenate from other selenium compounds that may occur or be added to animal feed premixes. Similarly such a method would permit distinguishing among like generic drugs or nutrients from different sources.

As a means of accomplishing the above, Applicant disclosed for the first time in U.S. Pat. No. 4,152,271 a ferromagnetic tracer particle which could be separated from the bulk mix much faster and easier than prior tracers by means of magnetic separators. The various advantages inherent in the use of such materials became readily apparent. It was noted that the use of the tracer in conjunction with a magnetic separator permitted examination of large samples of bulk materials avoiding the restriction to small samples required when sedimentation separation procedures were employed.

The vehicle for the tracer disclosed in Applicant's prior U.S. Pat. No. 4,152,271 was taught to consist of ground, soft iron or other ferromagnetic material that could be magnetized by a magnetic field, but which would lose its magnetism in the absence of such a field. The ferromagnetic particle was made easily identifiable by having an FD & C Color or other permitted distinguishable microingredient adsorbed on the ferromagnetic material. Since the tracer particles were to be counted, even major losses of the distinguishing adsorbed layer to the bulk material by abrasion or diffusion could be tolerated without loss of accuracy in the particle count.

It is the object of the present invention to incorporate the microingredient within the particle itself so that in separating the particle from the bulk material essentially 100% of the specific microingredient would also be separated and thus freed from the bulk material.

It is a further object of the present invention to provide a tracer particle which could carry a microingredient in a bulk mixture and yet could be retrieved for analytical testing with the assurance that substantially none of the microingredient had inadvertently separated from the tracer.

SUMMARY OF THE INVENTION

A tracer particle for determining the concentration of a microingredient in a bulk material is disclosed. The tracer particle comprises a finely divided ferromagnetic particulate material approximately 90% of which is approximately 325 mesh or smaller, a microingredient and a binder wherein the microingredient and ferromagnetic material are entrapped in the binder and wherein the tracer particle is approximately 35 to 80 mesh in size.

DETAILED DESCRIPTION OF THE INVENTION

As previously noted, the microingredient may be a drug, an essential nutrient, or other critical ingredient requiring analysis for quality control or for regulatory purposes. Magnetic retrieval of the tracer containing the microingredient from a bulk material can be accomplished in a relatively clean form free from the analytical interferences generally contributed by the bulk material itself. The specific tracer, when separated, can be easily identified either through chemical analysis or by physical means by employing a color coding of the tracer particle.

The ferromagnetic material may be reduced iron, electrolytic iron or other ferromagnetic material that can be magnetized by a magnetic field, but which loses its magnetism in the absence of such a field. The particular ferromagnetic material must be much smaller in size than the tracer particles so that each tracer particle can contain an amount sufficient to permit magnetic retrieval of the tracer. As such, as little as 10% of the ferromagnetic material can be employed in the tracer. However, for separation by techniques such as those disclosed in Applicant's prior patents, the tracer particles should contain approximately 25 to 35% of the ferromagnetic material, as a preferred embodiment, which results in a better than 90% recovery of the particle from the bulk mix. By practicing the mason jar technique disclosed in U.S. Pat. No. 4,152,271, the following data represents the percentage recovery of the tracer as a function of its iron content.

| Percent Iron | Percent Recovery |
| --- | --- |
| 4% | 1.0% |
| 8% | 7.9% |
| 16% | 18.5% |
| 25% | 90.9% |
| 32% | 95.1% |

The ferromagnetic material should preferably be relatively fine with at least 90% of the ferromagetic particles passing through a U.S. standard 325 mesh screen. By using particles of such a fine size, the composite tracer will have a reasonably proportionate share of the ferromagnetic material in each particulate member.

To aid in visual inspection, as a preferred embodiment, a color coding additive could be employed in the composite tracer. Various inert color-coding additives, such as dyed alumina or starch granules, can be employed. A preferred additive consists of finely divided silica gel, approximately 170 to 325 mesh, dyed with an FD&C color.

It is the intent of the present invention to provide a tracer whereby the various components such as the ferromagnetic material and microingredient are entrapped in a binder matrix. Typically, gelatin or cooked starch such as that used in the manufacture of granules preparatory to the pressing of pharmaceutical or other tablets are illustrative of suitable binders. For applications other than foods or animal feeds, synthetic plastics, acrylics or epoxies can be employed as binder materials.

A preferred material serving as a binder and matrix is a patent, straight or clear wheat flour containing at least 10% protein. Standard pasta manufacturing equipment can be used to mix a dough containing the required ingredients, to extrude the dough either as thin sheets or as vermicelli and to dry the extruded dough. This then is crumbed, ground in a hammer mill and screened to yield the subject tracer. Preferably, screening should be carried out so that the tracer particles are between approximately 35 and 80 mesh in size. The fines and coarse fractions can then generally be recycled. In such a size range, the tracer product will contain between approximately 50,000 to 70,000 discrete particles per gram.

EXAMPLE 1

The following ingredients were mixed in a typical domestic electric mixer:
flour (all purpose): 321.1 g
reduced iron (325 mesh): 125 g
silica gel (red): 10 g
A solution of 43.9 g sodium selenite was dissolved in 160 mls water and was added to the above and mixing continued resulting in an extremely stiff (dry) dough. On an as-received moisture basis, the mix was found to contain 500 g of "dry" material of which 25% was reduced iron, 2% color-coded silica gel and 8.78% sodium selenite (4.0% selenium).

The dough was then extruded through a meat grinder equipped with a 3/32" face plate and the extruded dough was then dried to approximately 10% miosture, then passed through a hammer mill equipped with a 1/16" screen. The output of the hammermill was then screened. Recovery of product between the sizes 35 to 80 mesh was 30%. There were 62.8 particles per milligram of finished product.

EXAMPLE 2

10 mg of the tracer produced pursuant to Example 1 was mixed with 100 g of a poultry mash to make a selenium pre-mix containing 100 parts per million tracer which is equivalent to 4 parts per million selenium as sodium selenite. A magnetic separator was employed which recovered 9.1 mg on a single pass. The 9.1 mg of recovered tracer was dispersed in 15 mls water, which was then filtered and a 10.0 ml aliquote was added to a flask containing approximately 20.0 mls of 0.0075 N sodium thiosulfate and then mixed. Three drops of 1% starch was added as an indicator after which 1 ml of 5% hydrochloric acid was added and the solution was immediately titrated with 0.005 N iodine.

As the selenite forms a stable complex with the thiosulfate, excess thiosulfate was back titrated with iodine and the pre-mix found to contain 3.6±0.02 ppm selenium.

Although such a simple and rapid titrimetric assay procedure is not generally applicable to complex matrices such as animal feeds or pre-mixes, such an assay is workable here since the analyte has been separated from the feed pre-mix in a comparatively clean form. Since selenium, although an essential nutrient, is extremely toxic at levels as low as 13 to 40 times its nutritional level, the Food & Drug Administration requires assays of each batch of selenium pre-mix to minimize the risk of catastrophic errors. By practicing the present invention, a simple, rapid, specific and inexpensive assay for such microingredients is possible.

Its extension to include other microingredients normally difficult to assay such as nicarbazin and vitamins K and D will be evident, as will its extension to differentiate like proprietary products of different manufacture.

I claim:

1. A tracer particle for determining the concentration of a microingredient in a bulk material, said tracer particle comprising a finely divided ferromagnetic particulate material approximately 90% of which is approximately 325 mesh or smaller, a microingredient and a binder wherein said microingredient and ferromagnetic material are entrapped in said binder and wherein said tracer particle is approximately 35 to 80 mesh in size.

2. The tracer particle of claim 1 wherein said ferromagnetic particulate material is present in said tracer particle in an amount between approximately 25 to 35% by weight.

3. The tracer particle of claim 1 which further comprises a color coding additive.

4. The tracer of claim 1 wherein said microingredient comprises selenium as sodium selenite or sodium selenate.

5. The tracer of claim 1 wherein said binder comprises a member selected from the group consisting of flour, gelatin, starch, plastics, acrylics and epoxies.

6. The tracer of claim 3 wherein said color coding additive comprises colored silica gel.

7. The tracer of claim 3 wherein said color coding additive comprises finely divided particles approximately 170 to 325 mesh in size.

8. A composition of matter in the form of a generally homogeneous admixture, said admixture being comprised of a major portion of a bulk ingredient and a minor portion of a tracer particle, said tracer particle comprising a finely divided ferromagnetic material approximately 90% of which is approximately 325 mesh or smaller, a microingredient and a binder wherein said microingredient and ferromagnetic material are entrapped in said binder and wherein said tracer particle is approximately 35 to 80 mesh in size.

9. The composition of claim 8 wherein said ferromagnetic particulate material is present in said tracer particle in an amount between approximately 25 to 35% by weight.

10. The composition of claim 8 wherein said tracer particle further comprises a color coding additive.

11. The composition of claim 8 wherein said microingredient is a drug.

12. The composition of claim 8 wherein said microingredient comprises selenium as sodium selenite or sodium selenate.

13. The composition of claim 8 wherein said binder comprises a member selected from the group consisting of flour, gelatin, starch, plastics, acrylics and epoxies.

14. The composition of claim 10 wherein said color coding additive comprises colored silica gel.

15. The composition of claim 10 wherein said color coding additive comprises finely divided particles approximately 170 to 325 mesh in size.

* * * * *